(12) United States Patent
Chai et al.

(10) Patent No.: US 6,473,643 B2
(45) Date of Patent: Oct. 29, 2002

(54) METHOD AND APPARATUS FOR MEASURING BODY FAT

(75) Inventors: Sunny Chai; Frederick C. Cha, both of Hong Kong (HK)

(73) Assignee: Fook Tin Plastic Factory, Ltd., Hong Kong (HK)

( * ) Notice: Subject to any disclaimer, the term of this patent is extended or adjusted under 35 U.S.C. 154(b) by 46 days.

(21) Appl. No.: 09/968,727

(22) Filed: Oct. 1, 2001

(65) Prior Publication Data

US 2002/0062090 A1 May 23, 2002

Related U.S. Application Data

(60) Provisional application No. 60/239,469, filed on Sep. 30, 2000.

(51) Int. Cl.[7] .................................................. A61B 5/00
(52) U.S. Cl. ..................................................... 600/547
(58) Field of Search ................................ 600/546, 547, 600/587

(56) References Cited

U.S. PATENT DOCUMENTS

| | | | |
|---|---|---|---|
| 4,895,163 A | 1/1990 | Libke et al. | 128/734 |
| 4,911,175 A | 3/1990 | Shizgal | 128/734 |
| 4,947,862 A | 8/1990 | Kelly | 128/734 |
| 4,949,727 A | 8/1990 | Yamazaki et al. | 128/734 |
| 5,086,781 A | 2/1992 | Bookspan | 128/734 |
| 5,203,344 A | 4/1993 | Scheltinga et al. | 128/734 |
| 5,335,667 A | 8/1994 | Cha et al. | 128/734 |
| 5,372,141 A | 12/1994 | Gallup et al. | 128/734 |
| 5,415,176 A | 5/1995 | Sato et al. | 128/734 |
| 5,449,000 A | 9/1995 | Libke et al. | 128/734 |
| 5,579,782 A | 12/1996 | Masuo | 128/734 |
| 5,611,351 A | 3/1997 | Sato et al. | 128/734 |
| 5,615,689 A | 4/1997 | Kotler | 128/630 |
| 5,720,296 A | 2/1998 | Cha | 128/734 |
| 5,722,396 A | 3/1998 | Kotler et al. | 128/34 |
| 5,817,031 A | 10/1998 | Masuo et al. | 600/547 |
| 5,840,042 A | 11/1998 | Arpadi et al. | 600/547 |
| 6,151,523 A | 11/2000 | Rosell Ferrer et al. | 600/547 |

OTHER PUBLICATIONS

Henry C. Lukaski, et al. "Validation of tetrapolar bioelectrical impedence method to assess human body composition" In Journal of Applied Physiology, 1986, pp. 1327–1332.

Christopher Nuñez et al., "Bioimpedance analysis: Evaluation of leg–to–leg system based on pressure contact foot–pad electrodues" in Official Journal of the American College of Sports Medicine, 1997, pp. 524–530.

*Primary Examiner*—Max Hindenburg
(74) *Attorney, Agent, or Firm*—Pennie & Edmonds LLP

(57) ABSTRACT

An improved apparatus and method are provided for measuring body fat of a live subject. The apparatus comprises a current source connected in parallel with two or more reference resistors and with the subject's body. The connections to the body are made via an array of electrodes. The resistors and the subject's body are switched in and out of the circuit, and the various voltages across the resistors and the body are detected by a voltage drop measuring device and input to an analog-to-digital convertor (ADC). The output from the ADC is presented to a microprocessor control unit, which calculates (1) the impedance of the individual's body based upon the various voltage measurements, and (2) the percent body fat as a function of that impedance and other ariables such as height, weight, age, and sex.

20 Claims, 2 Drawing Sheets

METHOD AND APPARATUS FOR MEASURING BODY FAT

This application claims the benefit under 35 U.S.C. § 119 of U.S. Provisional Patent Application No. 60/239,469 filed Sep. 30, 2000.

FIELD OF THE INVENTION

The present invention relates to an improved method and apparatus for measuring the body fat of a live subject, and more particularly, of a living human being.

BACKGROUND OF THE INVENTION

Body composition, and in particular percent body fat, is a well-recognized measure of physical health. Various techniques of determining percent body fat are presently in use, including caliper measurements, underwater displacement measurement, and bioelectrical impedance measurement.

In this last technique, as described in U.S. Pat. Nos. 5,415,176 and 5,611,351, both to Sato et al., a live subject whose body fat is to be measured stands upon a scale-like device with four electrodes mounted on its upper surface. A 50 kHz, 800 microampere electric current is produced by constant current source. This current is passed first through two electrodes in contact with the subject's toes and then through two reference resistors located in series with the subject's body and with each other. The electric current flowing through the subject causes a voltage potential to develop across the subject's heels.

Using a microprocessor-controlled switch array and a voltage measuring circuit, the heel-to-heel voltage is measured via two other electrodes in contact with the subject's heels. The voltages across the reference resistors are also measured while the electric current is applied to the subject's toes. A comparison of the voltages measured across the reference resistors with the heel-to-heel voltage provides a highly accurate measure of the heel-to-heel impedance. After certain additional parameters such as age, weight, and height are entered into the microprocessor, it calculates body density using an algorithm relating body impedance and the additional parameters to body density. Once body density is obtained, the microprocessor performs a second calculation to convert body density to percent body fat.

The present inventors have identified several disadvantages of the device taught by Sato et al. First, the 800 microampere current produces a relatively strong electric field that is centered on the current-supply electrodes. This field distribution restricts the location of the current-supply electrodes with respect to the voltage-detecting electrodes: the two sets of electrodes are required to be at least 5 cm apart. This distance limitation can present a problem in the body fat measurement of small children.

Second, the electrodes in the device of Sato et al. are flat and quite large, to accommodate a range of adult feet sizes. The pressure of the subject's weight on his feet, which are in contact with the wide, flat surface of the electrodes, restricts blood flow to the tissues above the electrodes. It is believed that this constriction causes the measured body impedance to be artificially increased, creating a source of error in the body fat measurement. Furthermore, the large electrodes of the device of Sato et al. causes the equipment to appear clinical and unaesthetic, and not at all user-friendly.

Third, the reference resistors in the device of Sato et al. are placed in series with each other and with the subject's body. This configuration limits the device's durability and reliability, for if the connection between any of the resistors or the current supply electrodes is accidentally broken, the device becomes entirely unable to function. In addition, the device is only capable of measuring combinations of reference resistors which are adjacent to each other. This arrangement thus limits the resolution of the measurement.

Finally, the current-supply electrodes in the device of Sato et al. contact the subject's toes, while the voltage-measurement electrodes contact his heels. Thus, the current flows from the toes through the feet toward the heels and then up through the legs. The measured body impedance thus includes the toe-heel impedance of each foot. Because toe-heel impedance is not included as an independent variable in most equations correlating body impedance and percent body fat, however, variations in foot size and foot impedance from subject to subject introduce additional error in the body fat calculation.

SUMMARY OF THE INVENTION

Accordingly, it is an object of the invention to overcome these and other problems associated with the prior art, and to provide an accurate, robust, high-resolution body fat analyzer that may be used by a wide range of subjects.

In accordance with one embodiment of the present invention, a subject's body composition is measured by (1) supplying a 50 kHz, 300 microampere electrical current to the subject's body via a group of current-supply electrodes that contact the subject's heels, (2) measuring the voltage across a group of voltage-detecting electrodes that contact the balls (and/or toes) of the subject's feet and across a plurality of internal reference resistors connected in parallel with the subject's body, and (3) calculating from these measurements the body fat percentage as a function of body impedance.

A preferred embodiment of the invention comprises a current source connected in parallel with two or more reference resistors and with the subject's body. The resistors and the subject's body are switched in and out of the circuit, and the various voltages across the resistors and the body are detected by a differential amplifier. The output of the differential amplifier is conditioned by a rectifier and low-pass filter and input to an analog-to-digital convertor (ADC). The output from the ADC is presented to a microprocessor control unit, which calculates (1) the impedance of the individual's body based upon the various voltage measurements, and (2) the percent body fat as a function of that impedance and other variables such as height, weight, age, and sex.

Additionally, the electrodes in the present invention are preferably designed as an array of small round knobs raised slightly above the surface upon which they are mounted. The electrodes are grouped into four groups—two current-supply electrode groups that contact the right and left heels, and two voltage-detecting electrode groups that contact the balls of the feet. Because a current of only 300 microamperes is preferably used, rather than the more conventional 800 microamperes, the current-supply electrodes and the voltage-detecting electrodes may be quite close to each other. In a preferred embodiment, the electrodes in the current-supply group are separated from the electrodes in the voltage-detecting group by a distance as small as about 1 cm.

This electrode array configuration has a number of advantages over the prior art. First, the electrodes may be spaced sufficiently close together to allow even small-footed children to use the device. Second, the subject has great flexibility as to the specific location of his feet on the device. Lastly, since the subject's foot makes contact with a number of small electrodes distributed over the surface of the foot, the blood circulation in each foot is enhanced, as compared with the flat plate electrodes as described in the background above, and the measurement is rendered thereby more reproducible.

DETAILED DESCRIPTION OF THE INVENTION

Figure 1:
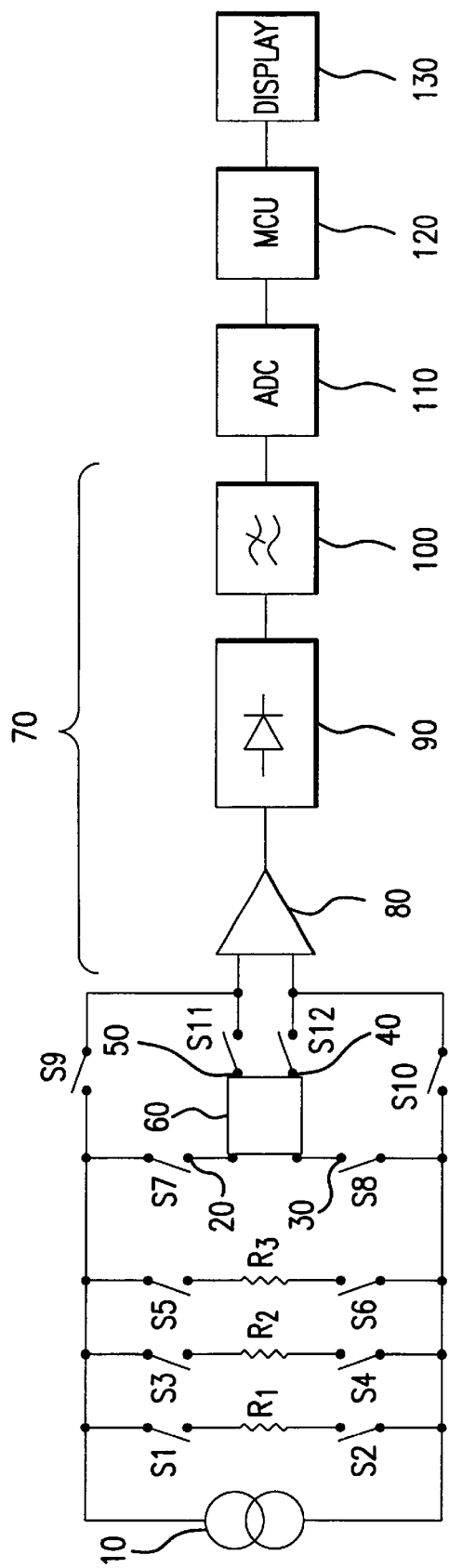
FIG. 1 is a block diagram illustrating a body fat analyzer embodying present invention.

A device embodying the present invention, as shown in a preferred embodiment in FIG. 1., comprises a 50 kHz, 300 microampere constant current source 10 connected in parallel with a plurality of reference resistors Ri (R1, R2, and R3 being shown as examples in FIG. 1) and with the subject's body 60. Resistors Ri and the subject's body 60 are switched in and out of the circuit by switches Sj (S1 through S8 in the embodiment shown in FIG. 1), which are controlled by microprocessor control unit ("MCU") 120. In the embodiment shown in FIG. 1, the various voltages across the resistors and the body are connected sequentially to voltage drop measuring device 70 via switches S9 through S12, also controlled by MCU 120.

For example, to measure the voltage developed across body 60, switches S7, S8, S11, and S12 are closed, while switches Si through S6, S9 and S10 are opened. Thus, current flows through the current-supply electrode group 20, which is in contact with one of the subject's heels, through body 60 and through the current-supply electrode group 30 in contact with the subject's other heel. Simultaneously, the voltage generated between the balls of the subject's feet is passed through voltage-detecting electrode groups 40 and 50, which are in contact with the balls of the subject's feet, to the inputs of voltage drop measuring device 70. Similarly, to measure the voltage developed across resistor R1, switches S1, S2, S9, and S10 are closed, while switches S3 through S8, S11, and S12 are opened. In this way, the voltage across any of the resistors or the subject's body may be measured.

Additionally, combinations of the references resistors Ri (R1, R2, and R3 in FIG. 1) and body 60 can be connected and the voltage across the combination measured. For example, resistors R1 and R2 can be connected by closing switches S1, S2, S3, S4, S9, and S10, and opening the other switches. Thus, a large number of resistance/voltage data points with a narrow resolution of resistance values can be obtained. Furthermore, the number of potential data points can readily be increased by increasing the number of reference resistors Ri in parallel with body 60. The resolution of the data points is set by the values of the reference resistors and the equivalent resistances of groups of resistors; the reference resistors are selected such that the full range of body impedance, which is typically 0 to 1000 ohms, is bracketed.

Since the voltages presented to voltage drop measuring device 70 are small AC voltages, voltage drop measuring device 70 comprises a differential amplifier 80 to amplify the AC voltage signal, a rectifier circuit 90, and a low pass filter (LPF) 100. Voltage drop measuring device 70 thus presents a DC voltage corresponding to the amplitude of the AC voltage signal to analog-to-digital convertor (ADC) 110, which in turn passes the digitized voltage measurement to MCU 120. MCU 120 then interpolates the body impedance by comparing the measured body voltage with the measured reference resistances. In this way, voltage measurement errors caused by contact resistances or amplifier nonlinearities are eliminated.

Next, MCU 120 uses a formula to calculate the percent body fat from the measured body impedance. In U.S. Pat. No. 5,415,176, Sato et al. teaches one such formula, a two-step calculation process in which body density is calculated first as a function of body impedance, and percent body fat is then calculated as a function of body density. The disclosed formula for the first calculation step is:

$$BD = 1.1144 - \frac{0.0976 * W * Z}{H^2} + 0.00084 * Z$$

where BD is body density, W is weight in kilograms, Z is body impedance, and H is height in centimeters. The formula disclosed for the second step is:

$$\% \ BF = \frac{4.57}{BD} - 4.142 * 100$$

where %BF is percent body fat and BD is body density. However, any formula relating body impedance to body fat may be used. Once MCU 120 calculates the body fat of the subject, it displays the results on a display screen 130.

Figure 2A:
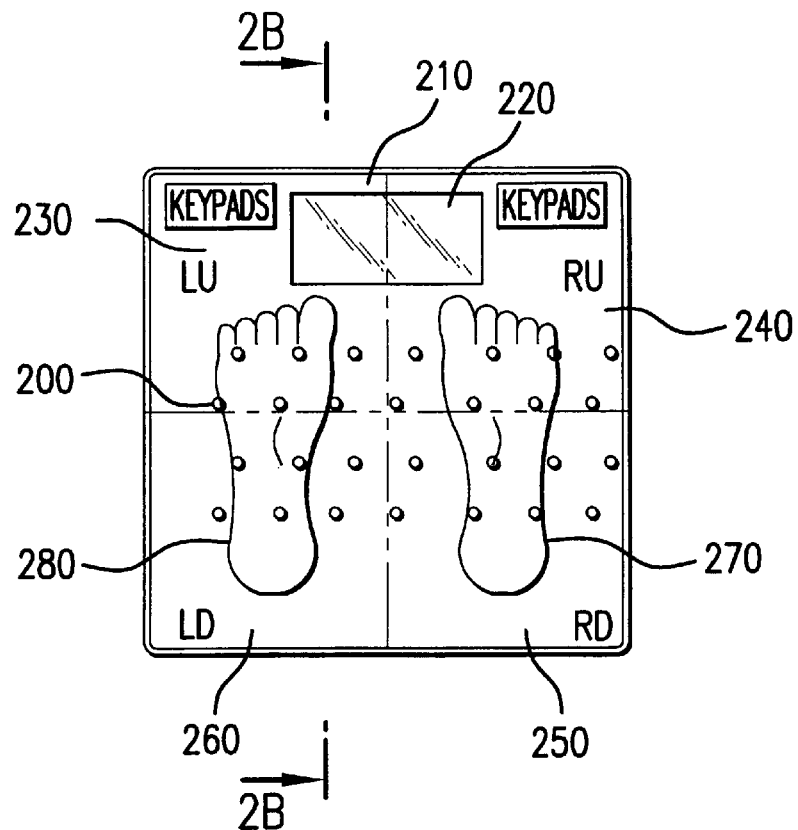
FIG. 2A illustrates a top-view of an electrode array mounted upon the upper surface of a body fat analyzer embodying the present invention.
Figure 2B:
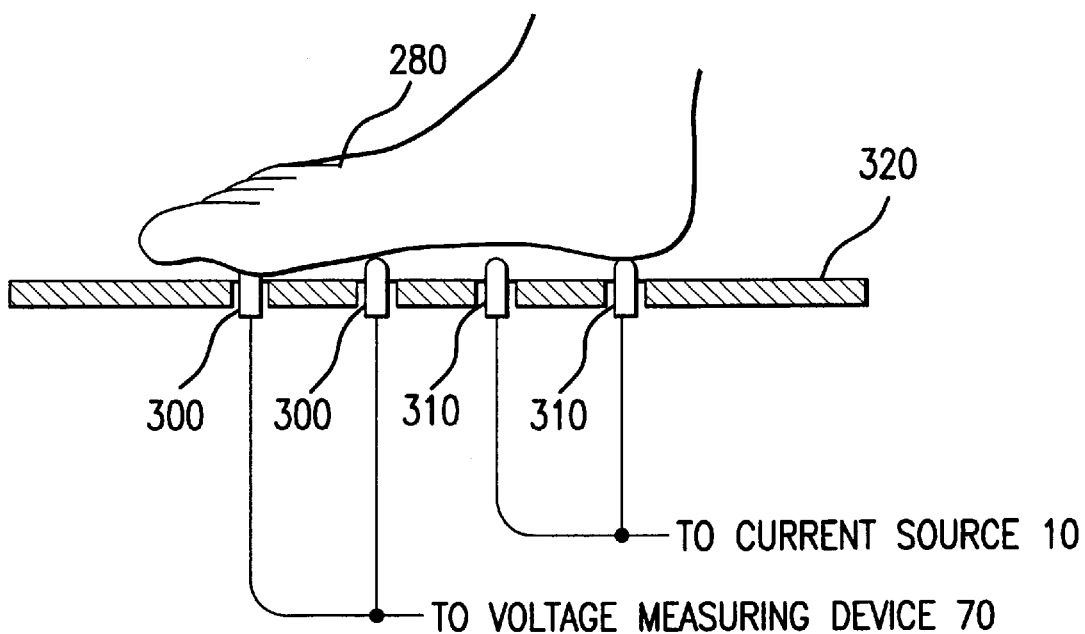
FIG. 2B illustrates a cross-sectional view of the device shown in FIG. 2A.

FIGS. 2A and 2B illustrate the electrode array configuration in a preferred embodiment of the invention. When the subject stands on the body fat analyzer, the feet 270, 280 rest on the discrete electrodes. In the specific embodiment illustrated, the electrodes are divided into four groups 230, 240, 250, and 260. Groups 230 and 240 are voltage-detecting electrodes, while groups 250 and 260 are current-supply electrodes. Compared with large flat electrodes, these discrete-geometry electrode groups stimulate the subject's feet, improving blood circulation and rendering the body impedance measurement more reproducible. Additionally, the subject is not restricted in the placement of his feet 270, 280, so long as the heel of the foot, 280 for example, contacts at least one of the electrodes in current-supply electrode group 260 and the ball of the foot 280 contacts at least one of the electrodes in voltage-detecting electrode group 230. In one embodiment, the electrodes of voltage-detecting groups 230, 240 and the electrodes of current-supply groups 250, 260 are separated by a distance of 1 cm, so that both children and adults can use the device. Also shown in FIG. 2A are the display panel 220 and a keypad 210 for entering parameters such as height, age, weight, and sex into the MCU.

FIG. 2B depicts a cross-sectional view through the body fat analyzer shown in FIG. 2A. For a given foot 280, voltage-detecting electrodes 300 contact the ball and toe of the foot, while current-supply electrodes 310 contact the heel. It may be seen from FIG. 2B that the voltage-detecting electrodes 300 are electrically connected, and that the current-supply electrodes 310 are electrically connected.

Preferably, non-conductive surface 320 is sufficiently rigid to support the weight of the subject without deforming, and may be made from any substantially rigid, nonconductive material, such as glass. Alternatively, conductive materials, such as aluminum, may also be used, as long as some gap or insulation is provided between the electrodes and surface 320.

While the invention has been described with reference to a specific embodiment, it will be appreciated by those of ordinary skill in the art that modifications can be made to the structure and form of the invention without departing from its spirit and scope. For example, it will be readily apparent to those of ordinary skill in the art that the electrode array configuration described above may be easily applied to body fat analyzers that use a two-point impedance measurement technique, rather than the four-point technique described above. So, too, it will be recognized that the arrangement of the reference resistors in parallel may also be applied to two-point measurement systems. It will further be apparent that although the electrodes in the present invention are described above as knob-shaped, they may also be configured as strips, bars, or any geometric shapes that do not substantially constrict blood flow to the surface of the foot. Accordingly, the scope of the invention is not limited to the embodiments described above, but is defined solely by the following claims.

What is claimed is:

1. A device for measuring the percent body fat of a subject's body, comprising:
   a. a housing;
   b. an array of five or more electrodes, mounted on said housing and arranged to contact such body,
   c. a current source connected to at least two electrodes in said array, whereby current may be supplied to such body, causing a voltage to develop across the body;
   d. a voltage amplifier connected to at least two electrodes in said array, whereby the voltage across said electrodes may be received and amplified; and
   e. a microprocessor, connected to said amplifier, and configured to compute the subject's percent body fat based on the amplified voltage;
   whereby said electrodes contact such body at discrete points, allowing largely-unrestricted blood flow at the surface of such body near said electrodes and thereby improving the reliability of the measurement.

2. The device of claim 1, wherein at least two of the electrodes in said array of five or more electrodes are electrically connected together.

3. The device of claim 1, wherein said array of electrodes includes:
   a. a first array of current-supply electrodes connected to said current source; and
   b. an second array of voltage-detecting electrodes connected to said voltage amplifier.

4. The device of claim 3, wherein the electrodes to which said current source is connected are in said first array, and wherein the electrodes to which said voltage amplifier is connected to are in said second array.

5. The device of claim 3, wherein each of the electrodes of said first array is mounted at least about one centimeter away from each of the electrodes in said second array.

6. The device of claim 3, wherein at least five of the five or more electrodes in said array serve as at least one of a current-supply electrode and a voltage-detecting electrode.

7. The device of claim 3, wherein
   a. the electrodes in said first array are grouped to form a first and a second group, and all of the electrodes in each group are electrically connected together, and each group is connected to said current source; and
   b. the electrodes in said second array are grouped into a third and a fourth group, all of the electrodes each group are electrically connected together, and each group is connected to said voltage amplifier.

8. The device of claim 7, wherein said housing has four quadrants, and each group of electrodes is mounted in one of said quadrants.

9. The device of claim 8, wherein said groups are arranged on said housing such that when such subject stands on said housing,
   a. said first and second groups contact the heels of his feet and
   b. said third and fourth groups contact the balls of his feet, whereby measurement errors caused by variations in heel-toe impedance are avoided.

10. The device of claim 1, wherein when such subject is in contact with said electrodes, an electrical current not greater in magnitude than about 300 microamperes flows through the subject's body.

11. The device of claim 10, wherein said current is about 300 microamperes.

12. The device of claim 1, wherein the surface of said housing is substantially rigid.

13. The device of claim 12, wherein the surface of said housing is glass.

14. A device for measuring the percent body fat of a subject's body, comprising:
   a. two or more voltage-detecting electrodes capable of contacting an extremity of such body;
   b. two or more current-supply electrodes capable of contacting such extremity at a location that is proximally closer to such body than that of the two or more voltage-detecting electrodes;
   c. a current source connected to said current-supply electrodes, whereby current may be supplied to such body;
   d. a voltage amplifier connected to said voltage-detecting electrodes, whereby a voltage across said such body may be received and amplified; and
   e. a microprocessor, configured to compute percent body fat based on the voltage detected by said voltage-detecting electrodes;
   whereby measurement errors caused by variations in the impedance of the extremity are reduced.

15. The device of claim 14, wherein
   a. said current-supply electrodes contact the heels of such subject's feet; and
   b. said voltage-detecting electrodes contact the balls of such subject's feet.

16. A device for measuring the percent body fat of a subject's body, comprising:
   a. two or more electrodes capable of contacting such body;
   b. two or more reference resistors arranged in parallel with such body;
   c. a current source;
   d. a voltage amplifier;
   e. a controllable switch, capable of connecting said current source and said voltage amplifier to said electrodes and to said reference resistors, such that current may be supplied to such body and said resistors and a voltage across them may be received and amplified; and
   f. a microprocessor, connected to said amplifier, and configured to compute the subject's percent body fat based on the amplified voltages;

whereby the device remains operational even if the connection to one of said reference resistors fails.

17. A method of measuring the percent body fat of a subject's body, comprising the steps of:
   a. sourcing current to at least two electrodes in an array of five or more electrodes contacting such body;
   b. receiving and amplifying a voltage across at least two electrodes in the array of electrodes; and
   c. calculating the subject's percent body fat based on the amplified voltage;
whereby the five or more electrodes contact such body at discrete points, allowing largely-unrestricted blood flow at the surface of such body near said electrodes and thereby improving the reliability of the measurement.

18. The method of claim 1, wherein at least two of the electrodes in said array of five or more electrodes are electrically connected together.

19. A method of measuring the percent body fat of a subject's body, comprising the steps of:
   a. sourcing a current through two or more current-supply electrodes contacting an extremity of such body;
   b. receiving and amplifying a voltage at two or more electrodes contacting such extremity at a location that is proximally more distant from the core of the body than that of the two or more current-supply electrodes; and
   c. calculating the subject's percent body fat based on the amplified voltage;
whereby measurement errors caused by variations in the impedance of the extremity are reduced.

20. A method of measuring the percent body fat of a subject's body, comprising the steps of:
   a. sourcing a current through two or more reference resistors arranged in parallel with the body;
   b. receiving and amplifying a voltage developed across one or more of the reference resistors;
   c. sourcing a current through two or more electrodes contacting the body;
   d. receiving and amplifying a voltage at two or more electrodes contacting the body;
   e. calculating the subject's percent body fat based on the received and amplified voltage;
whereby the device remains operational even if the connection to one of the reference resistors fails.

* * * * *

UNITED STATES PATENT AND TRADEMARK OFFICE
CERTIFICATE OF CORRECTION

PATENT NO. : 6,473,643 B2  Page 1 of 1
DATED : October 29, 2002
INVENTOR(S) : Chai et al.

It is certified that error appears in the above-identified patent and that said Letters Patent is hereby corrected as shown below:

Column 7,
Line 16, replace the numeral "1" with -- 17 --, so claim 18 reads:

18. The method of claim 17, wherein at least two of the electrodes in said array of five or more electrodes are electrically connected together.

Signed and Sealed this

Fourth Day of February, 2003

JAMES E. ROGAN
*Director of the United States Patent and Trademark Office*